(12) United States Patent
Freeman et al.

(10) Patent No.: US 12,207,953 B2
(45) Date of Patent: *Jan. 28, 2025

(54) ACUTE CARE TREATMENT SYSTEMS DASHBOARD

(71) Applicant: ZOLL Medical Corporation, Chelmsford, MA (US)

(72) Inventors: Gary A Freeman, Waltham, MA (US); Guy R Johnson, Wilton, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/358,997

(22) Filed: Jul. 26, 2023

(65) Prior Publication Data

US 2024/0090856 A1     Mar. 21, 2024

Related U.S. Application Data

(63) Continuation of application No. 16/824,763, filed on Mar. 20, 2020, now Pat. No. 11,759,152, which is a (Continued)

(51) Int. Cl.
*A61B 5/00*     (2006.01)
*A61B 5/0205*   (2006.01)
(Continued)

(52) U.S. Cl.
CPC .......... *A61B 5/7475* (2013.01); *A61B 5/0002* (2013.01); *A61B 5/0205* (2013.01);
(Continued)

(58) Field of Classification Search
None
See application file for complete search history.

(56) References Cited

U.S. PATENT DOCUMENTS

| 5,086,391 A | 2/1992 | Chambers |
| 5,218,969 A | 6/1993 | Bredesen et al. |

(Continued)

FOREIGN PATENT DOCUMENTS

| CN | 101226452 | 7/2008 |
| CN | 101779986 | 7/2010 |

(Continued)

OTHER PUBLICATIONS

Hernandez, et al., "C.A.U.S.E.: Cardiac Arrest Ultra-sound Exam—A Better Approach to Managing Patients in Primary Non-arrhythmogenic Cardiac Arrest," Resuscitation, vol. 76, Issue 2, pp. 198-206 (Feb. 2008).

*Primary Examiner* — Carl H Layno
*Assistant Examiner* — Manolis Pahakis
(74) *Attorney, Agent, or Firm* — ZOLL Medical Corporation

(57) ABSTRACT

A patient monitoring system includes at least one sensor configured to measure patient data including physiologic waveform data, a defibrillator configured to couple to the at least one sensor and including a touchscreen user interface, at least one processor communicatively coupled to the touchscreen user interface and configured to cause the touchscreen user interface to display the patient data including at least one physiologic waveform based on the physiologic waveform data, detect user input including a first user touchscreen input and a second user touchscreen input, define endpoints of a caliper based on the first user touchscreen input and the second user touchscreen input, wherein the endpoints of the caliper identify a particular portion of the at least one physiologic waveform, and cause the touchscreen to display a measurement of the particular portion of the at least one physiologic waveform based on the endpoints of the caliper.

17 Claims, 20 Drawing Sheets

Related U.S. Application Data continuation of application No. 16/399,827, filed on Apr. 30, 2019, now Pat. No. 10,959,683, which is a continuation of application No. 13/294,947, filed on Nov. 11, 2011, now Pat. No. 10,485,490.

(60) Provisional application No. 61/436,943, filed on Jan. 27, 2011, provisional application No. 61/413,266, filed on Nov. 12, 2010, provisional application No. 61/412,679, filed on Nov. 11, 2010.

(51) Int. Cl.

| | | |
|---|---|---|
| *A61B 5/024* | (2006.01) | |
| *A61B 5/08* | (2006.01) | |
| *A61B 5/113* | (2006.01) | |
| *A61B 5/145* | (2006.01) | |
| *A61B 5/318* | (2021.01) | |
| *A61B 7/00* | (2006.01) | |
| *A61N 1/39* | (2006.01) | |
| *G06F 1/16* | (2006.01) | |
| *G06F 3/01* | (2006.01) | |
| *G06F 3/04883* | (2022.01) | |
| *G16H 40/63* | (2018.01) | |
| *G16H 40/67* | (2018.01) | |
| *G16H 50/20* | (2018.01) | |

(52) U.S. Cl.
CPC ............. *A61B 5/318* (2021.01); *A61B 5/742* (2013.01); *G06F 3/017* (2013.01); *G06F 3/04883* (2013.01); *G16H 40/63* (2018.01); *G16H 40/67* (2018.01); *G16H 50/20* (2018.01); *A61B 5/02405* (2013.01); *A61B 5/0816* (2013.01); *A61B 5/1135* (2013.01); *A61B 5/14532* (2013.01); *A61B 5/14539* (2013.01); *A61B 5/14542* (2013.01); *A61B 5/4824* (2013.01); *A61B 7/00* (2013.01); *A61B 2505/01* (2013.01); *A61B 2560/0456* (2013.01); *A61N 1/3904* (2017.08); *A61N 1/3925* (2013.01); *A61N 1/3993* (2013.01); *G06F 1/1632* (2013.01); *G06F 2203/04806* (2013.01)

(56) References Cited

U.S. PATENT DOCUMENTS

| | | | |
|---|---|---|---|
| 5,255,187 A | 10/1993 | Sorensen | |
| 5,626,151 A | 5/1997 | Linden | |
| 5,664,571 A | 9/1997 | Yamazaki | |
| 5,782,878 A | 7/1998 | Morgan et al. | |
| 5,813,403 A | 9/1998 | Soller et al. | |
| 5,853,005 A | 12/1998 | Scanlon | |
| 6,024,699 A | 2/2000 | Surwit et al. | |
| 6,025,699 A | 2/2000 | Cummings | |
| 6,055,447 A | 4/2000 | Weil et al. | |
| 6,261,238 B1 | 7/2001 | Gavriely | |
| 6,270,456 B1 | 8/2001 | Iliff | |
| 6,321,113 B1 | 11/2001 | Parker et al. | |
| 6,440,082 B1 | 8/2002 | Joo et al. | |
| 6,443,889 B1 | 9/2002 | Groth et al. | |
| 6,488,629 B1 | 12/2002 | Saetre et al. | |
| 6,551,243 B2 | 4/2003 | Bocionek et al. | |
| 6,564,088 B1 | 5/2003 | Soller et al. | |
| 6,572,560 B1 | 6/2003 | Watrous et al. | |
| 6,629,937 B2 | 10/2003 | Watrous | |
| 6,725,447 B1 | 4/2004 | Gilman et al. | |
| 6,766,188 B2 | 7/2004 | Soller | |
| 6,786,917 B1 | 9/2004 | Schiller et al. | |
| 6,829,501 B2 | 12/2004 | Nielsen et al. | |
| 6,849,045 B2 | 2/2005 | Iliff | |
| 6,898,462 B2 * | 5/2005 | Rock .................... | A61N 1/3993 607/9 |
| 7,020,844 B2 | 3/2006 | Trevino et al. | |
| 7,072,840 B1 | 7/2006 | Mayaud | |
| 7,107,095 B2 | 9/2006 | Manolas | |
| 7,164,945 B2 | 1/2007 | Hamilton et al. | |
| 7,184,963 B1 | 2/2007 | Shannon | |
| 7,212,128 B2 | 5/2007 | Schenker | |
| 7,213,009 B2 | 5/2007 | Pestotnik et al. | |
| 7,306,560 B2 | 12/2007 | Iliff | |
| 7,421,647 B2 | 9/2008 | Reiner | |
| 7,447,643 B1 | 11/2008 | Olson et al. | |
| 7,549,961 B1 | 6/2009 | Hwang | |
| 7,558,622 B2 | 7/2009 | Tran | |
| 7,706,878 B2 * | 4/2010 | Freeman .................. | A61G 7/07 607/6 |
| 7,742,931 B2 | 6/2010 | McElwain Miller | |
| 7,835,925 B2 | 11/2010 | Roe et al. | |
| 7,841,986 B2 | 11/2010 | He et al. | |
| 7,853,327 B2 | 12/2010 | Patangay et al. | |
| 7,945,452 B2 | 5/2011 | Fathallah et al. | |
| 7,986,309 B2 | 7/2011 | Kim | |
| 8,068,104 B2 | 11/2011 | Rampersad | |
| 8,098,423 B2 | 1/2012 | Islam | |
| 8,137,270 B2 | 3/2012 | Keenan et al. | |
| 8,335,694 B2 | 12/2012 | Reiner | |
| 8,337,404 B2 | 12/2012 | Osorio | |
| 8,352,021 B2 | 1/2013 | Scheib | |
| 8,355,928 B2 | 1/2013 | Spahn | |
| 8,388,545 B2 | 3/2013 | Keren et al. | |
| 8,392,217 B2 | 3/2013 | Iliff | |
| 8,414,498 B2 | 4/2013 | Keren et al. | |
| 8,487,881 B2 | 7/2013 | Keenan | |
| 8,510,126 B2 | 8/2013 | Martin et al. | |
| 8,527,049 B2 | 9/2013 | Koh et al. | |
| 8,587,426 B2 | 11/2013 | Bloem | |
| 8,744,543 B2 | 6/2014 | Li et al. | |
| 8,790,257 B2 | 7/2014 | Libbus et al. | |
| 8,900,141 B2 | 12/2014 | Smith et al. | |
| 8,923,918 B2 | 12/2014 | Kreger et al. | |
| 8,956,292 B2 * | 2/2015 | Wekell ................ | G06F 3/04817 600/301 |
| 9,153,112 B1 | 10/2015 | Kiani et al. | |
| 9,286,440 B1 | 3/2016 | Carter et al. | |
| 9,492,084 B2 | 11/2016 | Behar et al. | |
| 9,596,989 B2 | 3/2017 | Morris | |
| 9,658,756 B2 | 5/2017 | Freeman et al. | |
| 10,303,852 B2 | 5/2019 | Peterson et al. | |
| 10,410,748 B2 | 9/2019 | Fitzgerald et al. | |
| 2001/0047140 A1 | 11/2001 | Freeman | |
| 2002/0151812 A1 * | 10/2002 | Scheiner ................ | A61B 5/742 600/528 |
| 2002/0184055 A1 | 12/2002 | Naghavi et al. | |
| 2003/0036683 A1 | 2/2003 | Kehr et al. | |
| 2003/0036924 A1 | 2/2003 | Rosen et al. | |
| 2004/0049233 A1 | 3/2004 | Edwards | |
| 2004/0064169 A1 | 4/2004 | Briscoe et al. | |
| 2004/0064342 A1 | 4/2004 | Browne et al. | |
| 2004/0143298 A1 | 7/2004 | Nova et al. | |
| 2004/0147818 A1 | 7/2004 | Levy et al. | |
| 2004/0152954 A1 * | 8/2004 | Pearce .................... | G09B 23/28 600/300 |
| 2004/0214148 A1 | 10/2004 | Salvino et al. | |
| 2005/0080336 A1 | 4/2005 | Byrd et al. | |
| 2005/0187472 A1 | 8/2005 | Lysyansky et al. | |
| 2005/0277872 A1 | 12/2005 | Colby et al. | |
| 2006/0026535 A1 * | 2/2006 | Hotelling ............... | G06F 3/0488 715/863 |
| 2006/0047188 A1 | 3/2006 | Bohan | |
| 2006/0111933 A1 | 5/2006 | Wheeler | |
| 2006/0116908 A1 | 6/2006 | Dew et al. | |
| 2006/0122864 A1 | 6/2006 | Gottesman et al. | |
| 2006/0142648 A1 | 6/2006 | Banet et al. | |
| 2006/0259080 A1 * | 11/2006 | Vaisnys ................ | A61N 1/3904 607/5 |
| 2006/0270952 A1 | 11/2006 | Freeman et al. | |
| 2007/0032830 A1 | 2/2007 | Bowers | |
| 2007/0175980 A1 | 8/2007 | Alsafadi | |
| 2007/0191687 A1 | 8/2007 | Justus | |
| 2007/0219588 A1 * | 9/2007 | Freeman ................ | A61N 1/3993 607/5 |

(56) References Cited

U.S. PATENT DOCUMENTS

| | | | |
|---|---|---|---|
| 2007/0252821 A1* | 11/2007 | Hollemans | G06F 3/0488 345/173 |
| 2007/0255115 A1 | 11/2007 | Anglin et al. | |
| 2008/0004663 A1* | 1/2008 | Jorgenson | A61N 1/3904 607/32 |
| 2008/0015439 A1 | 1/2008 | Raju et al. | |
| 2008/0077010 A1 | 3/2008 | Cohen-Solal et al. | |
| 2008/0176199 A1* | 7/2008 | Stickney | A61B 5/0535 600/509 |
| 2008/0188765 A1* | 8/2008 | Stolarski | A61B 5/363 600/518 |
| 2009/0018449 A1 | 1/2009 | Raju | |
| 2009/0024175 A1* | 1/2009 | Freeman | G09B 23/288 607/6 |
| 2009/0054735 A1 | 2/2009 | Higgins et al. | |
| 2009/0054743 A1* | 2/2009 | Stewart | G06T 11/206 600/301 |
| 2009/0069642 A1 | 3/2009 | Gao et al. | |
| 2009/0076345 A1 | 3/2009 | Manicka et al. | |
| 2009/0089095 A1 | 4/2009 | Esham et al. | |
| 2009/0150184 A1 | 6/2009 | Spahn | |
| 2009/0227883 A1 | 9/2009 | Zhang et al. | |
| 2009/0270931 A1 | 10/2009 | Liden | |
| 2010/0010319 A1 | 1/2010 | Tivig et al. | |
| 2010/0030094 A1 | 2/2010 | Stig | |
| 2010/0087883 A1 | 4/2010 | Sullivan et al. | |
| 2010/0152801 A1 | 6/2010 | Koh et al. | |
| 2010/0161353 A1 | 6/2010 | Mayaud | |
| 2010/0249540 A1 | 9/2010 | Lisogurski | |
| 2010/0302281 A1 | 12/2010 | Kim | |
| 2010/0305412 A1 | 12/2010 | Darrah et al. | |
| 2011/0074831 A1 | 3/2011 | Lynch et al. | |
| 2011/0115814 A1* | 5/2011 | Heimendinger | G06T 11/206 345/173 |
| 2011/0118561 A1 | 5/2011 | Tari et al. | |
| 2011/0130636 A1 | 6/2011 | Daniel et al. | |
| 2011/0172550 A1* | 7/2011 | Martin | G16H 40/40 600/523 |
| 2011/0208540 A1 | 8/2011 | Lord et al. | |
| 2011/0283231 A1* | 11/2011 | Richstein | G06F 3/0488 715/810 |
| 2011/0295078 A1* | 12/2011 | Reid | G16H 40/67 600/300 |
| 2012/0075103 A1* | 3/2012 | Powell | A61B 5/349 702/19 |
| 2012/0123218 A1 | 5/2012 | Renes | |
| 2012/0180002 A1* | 7/2012 | Campbell | G06F 3/0485 715/863 |
| 2012/0278099 A1 | 11/2012 | Kelly et al. | |
| 2013/0023780 A1 | 1/2013 | Cardinale et al. | |
| 2013/0060156 A1 | 3/2013 | Gregg et al. | |
| 2013/0096649 A1 | 4/2013 | Martin et al. | |
| 2013/0124090 A1 | 5/2013 | Gotschall et al. | |
| 2014/0148719 A1* | 5/2014 | Yang | G06F 3/04883 600/523 |
| 2014/0296675 A1 | 10/2014 | Freeman et al. | |
| 2015/0359489 A1 | 12/2015 | Baudenbacher et al. | |

FOREIGN PATENT DOCUMENTS

| | | |
|---|---|---|
| CN | 101849241 | 9/2010 |
| JP | 09-262213 | 10/1997 |
| JP | 2003521972 | 7/2003 |
| JP | 2005524436 | 8/2005 |
| JP | 2005524498 | 8/2005 |
| JP | 2007125151 | 5/2007 |
| JP | 2008200111 | 9/2008 |
| WO | 20080086496 | 7/2008 |

* cited by examiner

DIFFERENTIAL DIAGNOSIS OF ACUTE DYSPNEA IN ADULTS

CARDIAC: CONGESTIVE HEART FAILURE, CORONARY ARTERY DISEASE, ARRHYTHMIA, PERICARDITIS, ACUTE MYOCARDIAL INFARCTION, ANEMIA

PULMONARY: CHRONIC OBSTRUCTIVE PULMONARY DISEASE, ASTHMA, PNEUMONIA, PNEUMOTHORAX, PULMONARY EMBOLISM, PLEURAL EFFUSION, METASTATIC DISEASE, PULMONARY EDEMA, GASTROESOPHAGEAL REFLUX DISEASE WITH ASPIRATION, RESTRICTIVE LUNG DISEASE

PSYCHOGENIC: PANIC ATTACKS, HYPERVENTILATION, PAIN, ANXIETY

UPPER AIRWAY OBSTRUCTION: EPIGLOTTITIS, FOREIGN BODY, CROUP, EPSTEIN-BARR VIRUS

ENDOCRINE: METABOLIC ACIDOSIS, MEDICATIONS

CENTRAL: NEUROMUSCULAR DISORDERS, PAIN, ASPIRIN OVERDOSE

PEDIATRIC: BRONCHIOLITIS, CROUP, EPIGLOTTITIS, FOREIGN BODY ASPIRATION, MYOCARDITIS

FIG. 5

CLUES TO THE DIAGNOSIS OF DYSPNEA

| SYMPTOMS OR FEATURES IN THE HISTORY | POSSIBLE DIAGNOSIS |
|---|---|
| COUGH | ASTHMA, PNEUMONIA |
| SEVERE SORE THROAT | EPIGLOTTITIS |
| PLEURITIC CHEST PAIN | PERICARDITIS, PULMONARY EMBOLISM, PNEUMOTHORAX, PNEUMONIA |
| ORTHOPNEA, NOCTURNAL PAROXYSMAL DYSPNEA, EDEMA | CONGESTIVE HEART FAILURE |
| TOBACCO USE | CHRONIC OBSTRUCTIVE PULMONARY DISEASE, CONGESTIVE HEART FAILURE, PULMONARY EMBOLISM |
| INDIGESTION, DYSPHAGIA | GASTROESOPHAGEAL REFLUX DISEASE, ASPIRATION |
| BARKING COUGH | CROUP |

FIG. 6

PHYSICAL EXAMINATION FINDINGS IN THE DIAGNOSIS OF ACUTE DYSPNEA

| FINDINGS | POSSIBLE DIAGNOSIS |
|---|---|
| WHEEZING, PULSUS PARADOXUS, ACCESSORY MUSCLE USE | ACUTE ASTHMA, COPD EXACERBATION |
| WHEEZING, CLUBBING, BARREL CHEST, DECREASED BREATH SOUNDS | COPD EXACERBATION |
| FEVER, CRACKLES, INCREASED FREMITUS | PNEUMONIA |
| EDEMA, NECK VEIN DISTENSION, $S_3$ OR $S_4$, HEPATOJUGULAR REFLUX, MURMERS, RALES, HYPERTENSION, WHEEZING | CONGESTIVE HEART FAILURE, PULMONARY EDEMA |
| WHEEZING, FRICTION RUB, LOWER EXTREMITY SWELLING | PULMONARY EMBOLISM |
| ABSENT BREATH SOUNDS, HYPERRESONANCE | PNEUMOTHORAX |
| INSPIRATORY STRIDOR, RHONCHI, RETRACTIONS | CROUP |
| STRIDOR, DROOLING, FEVER | EPIGLOTTITIS |
| STRIDOR, WHEEZING, PERSISTENT PNEUMONIA | FOREIGN BODY ASPIRATION |
| WHEEZING, FLARING, INTERCOSTAL RETRACTIONS, APNEA | BRONCHIOLITIS |
| SIGHING | HYPERVENTILATION |

COPD = CHRONIC OBSTRUCTIVE PULMONARY DISEASE

FIG. 7

1. Complete a scene size-up and determine if the scene is safe to approach. If the scene becomes unsafe at any time, withdraw.

2. Determine and evaluate the mechanism of injury.

3. Determine the number of patients and initiate MCI plan as appropriate.

4. Complete initial assessment according to initial assessment protocol, with attention to airway, breathing and circulation 5. Consider the need for spinal stabilization.

6. Determine the patient's level of consciousness by use of the AVPU scale
    a. A – Alert
    b. V – Responsive to verbal stimuli
    c. P – Responsive to painful stimuli
    d. U – Unresponsive 7. Assess vital signs.

8. Identify patient priority and need for ALS care. Dispatch ALS, if necessary.

9. Complete an appropriate secondary physical exam (see below):
    a. Rapid Trauma Exam: for patients with multi-system trauma or single-system trauma with a high index of suspicion for serious mechanism of injury (MOI).
    b. Focused physical exam: for patients with isolated injuries resulting from low index of suspicion for serious MOI who have no critical criteria according to dispatching ALS protocols.

10. Treat all life threatening injuries as found.

11. Complete history of event and past medical history using SAMPLE & OPQRST.

12. Treat all non-life threatening injuries as time allows.

13. Transport immediately.

FIG. 13

| RAPID TRAUMA ASSESSMENT |
|---|
| DETERMINE MOI |
| ABC'S |
| CONSIDER C-SPINE STABILIZATION |
| HEAD<br>DCAP – BTLS<br>EARS: BLEEDING, DISCHARGE, BRUISING BEHIND EARS<br>PUPILS: EQUALITY & REACTIVITY, RACCOON EYES, IMPALED OBJECTS<br>MOUTH: RE-CHECK AIRWAY, DENTURES, LOOSE OR BROKEN TEETH<br>OCCLUSIONS, BLEEDING, VOMITUS, GAG REFLEX, ASSESS BREATHING |
| NECK<br>DCAP – BTLS<br>JVD, TRACHEAL DEVIATION<br>C-SPINE: DEFORMITY OR TENDERNESS<br>ACCESSORY MUSCLE USE IN RESPIRATION<br>BLUNT TRAUMA<br>BURNS |
| CHEST<br>DCAP – BTLS<br>EQUAL CHEST RISE AND FALL<br>OPEN WOUNDS, AIR LEAKS<br>BREATH SOUNDS |
| ABDOMEN<br>DCAP – BTLS<br>PULSATING MASS<br>PALPATE FOUR QUADRANTS<br>TENDERNESS & GUARDING<br>DISTENTION<br>SIGNS OF PREGNANCY |
| PELVIS<br>DCAP – BTLS<br>ASSESS FOR INSTABILITY<br>PRIAPISM<br>BLEEDING OR DISCHARGE |
| EXTREMITIES<br>DCAP – BTLS<br>PULSE, MOVEMENT AND SENSATION |
| POSTERIOR<br>DCAP – BTLS<br>LUNG SOUNDS<br>SKIN WOUNDS OR LESIONS |

FIG. 14

| FOCUSED PHYSICAL EXAM |
|---|
| DETERMINE MOI |
| ABC'S |
| CONSIDER C-SPINE STABILIZATION |
| ASSESS THE AFFECTED AREA |
| ASSESS THE AREAS "ABOVE" AND "BELOW" THE AFFECTED AREA |

FIG. 15

1. Follow initial assessment and trauma assessment protocols for general guidelines on patient care.

2. Control all major bleeding according to standard BLS techniques.

3. Administer oxygen according to oxygen administration protocol.

4. Make every effort to locate and transport the amputated appendage with the patient.

5. Wrap the appendage in moist sterile dressing and place it in a plastic bag. Use ice packs or ice to keep the appendage cool.

6. If possible, contact Medical Control prior to transport to ensure appropriateness of transport destination.

FIG. 16

1. Assess the patient according to initial assessment and trauma assessment protocols.

2. Monitor and maintain a patent airway. Ensure adequate respirations; assist respirations via BVM if indicated.

3. Evaluate for and attempt control of any major bleeding immediately. Use the following steps to control major bleeding:
   a. Apply direct pressure
   b. Elevate wound above the level of the heart, if feasible
   c. Apply pressure at the pulse point proximal to the wound
   d. Apply ice or cold pack
   e. Apply tourniquet 2 inches above the wound and tighten until bleeding stops. Mark the time of application around or on the tourniquet.

4. If a puncture wound is found in the chest, stomach or on the back, take the following steps:
   a. Immediately cover wound with a gloved hand
   b. Apply direct pressure
   c. Place occlusive dressing over wound
   d. Tape on three sides
   e. Evaluate for lung sounds around the site of the wound in the case of chest, upper back or upper abdominal wounds 5. Provide oxygen via NRB mask.

6. Evaluate all minor wounds after ensuring ABC's, completing assessment and treating all life threatening emergencies.

7. Bandage all wounds using proper BLS technique.

FIG. 17

1. Follow initial assessment and trauma assessment protocols for general patient care guidelines.

2. Pay close attention to airway and breathing considerations. Always be aware of possible compromise to airway and breathing caused by burns to the airway.

3. Provide oxygen via NRB at 15 lpm. Assist respirations with BVM as necessary.

4. Remove all clothing or restricting items on or around the burned area(s) if possible.

5. Determine the degree and extent of burns using the "rule of nines" when appropriate. Document findings in PCR.

6. Cover burns with sterile dressings.

7. Keep the patient warm and guard against hypothermia.

8. For significant burn injuries, contact Medical Control for decision regarding transport to trauma center or designated burn center.

FIG. 18

1. Follow Scene Safety protocol. Ensure that electrical source has been turned off by appropriately trained professionals and there is no danger to the rescuers while providing care. Stage away from the patient until such time as adequate scene safety can be assured.

2. Follow initial assessment and trauma assessment protocols for general patient care guidelines.

3. Ensure adequacy of airway, breathing and circulation.

4. Provide oxygen via NRB at 15 lpm or assist via BVM attached to supplemental oxygen at 15 lpm.

5. If pulse is absent:
   a. Begin CPR and attach AED.
   b. Defibrillate with AED as indicated.
   c. Ensure patent airway.

6. Consider transport options and need for assessment at trauma center or designated burn center.

FIG. 19

The following algorithm outlines requirements and indications for spinal immobilization. It is based on the algorithm published in the Pre-hospital Trauma Life Support curriculum.

Use this algorithm to evaluate and treat patients with known or suspected head trauma, spinal injuries, or mechanism of injury (MOI) which might indicate a need for immobilization.

Use clinical judgment in all cases. Where concerns exist, contact online medical control or immobilize and initiate transport. Whenever in doubt, err on the side of caution and maintain cervical spine immobilization.

FIG. 20

1. Assess patient according to initial assessment and trauma assessment protocols. Perform a rapid trauma exam.

2. Ensure airway and adequate respiratory effort. Provide oxygen via NRB at 15 lpm or assist respirations via BVM.

3. Assess circulatory status for adequate pulse and signs of hypoperfusion. Control hemorrhaging with pressure.

4. Establish C-spine precautions and prepare to immobilize patient.

5. Determine level of consciousness using AVPU scale and assess for altered mental status.

6. Treat all life-threatening injuries as soon as possible.

7. Obtain a complete set of vitals. Monitor and reassess vital signs continuously.

8. Initiate transport to the closest appropriate facility immediately. Notify receiving facility en route. For assistance with transport decisions, contact Medical Control.

FIG. 22

1. Assess patient according to initial assessment and trauma assessment protocols. Make a special effort to determine the amount of time that the patient was in the water or submerged under water.

2. Open and maintain patent airway. Be ready to suction water from airway as necessary.

3. Check for spontaneous respirations and for pulse

4. If spontaneous respirations are present, provide high concentrations of oxygen by NRB mask according to oxygen administration protocol. Assist via BVM if respiratory effort is inadequate.

5. If spontaneous pulse and respirations are absent, refer to cardiac arrest protocols. Initiate advanced airway procedures and defibrillate as necessary.

6. Transport immediately. Contact Medical Control for assistance in determining appropriate receiving facility.

FIG. 23

1. Assess patient according to initial assessment and trauma assessment protocols. Perform a rapid trauma exam.

2. Ensure patent airway and adequate respiratory effort. Provide oxygen via NRB at 15 lpm or assist via BVM if needed.

3. Assess circulatory status for adequate pulse and signs of hypoperfusion.

4. Establish C-spine precautions and prepare to immobilize patient.

5. Determine level of consciousness (by use of the AVPU scale) and assess for altered mental status.

6. Treat all life-threatening injuries as soon as possible.

7. Obtain a complete set of vitals. Monitor and reassess vital signs continuously.

8. Initiate transport to the closest appropriate facility immediately. Contact Medical Control for assistance in selecting most appropriate receiving facility.

9. Transport patient on the patient's left side, left lateral recumbent position, or raise the left side of the backboard at an angle greater than 15 degrees using towels, blankets, head-blocks, etc. (unless the patient is in cardiac arrest).

FIG. 24

1. Assess and treat patient according to initial assessment and trauma assessment protocols.

2. Immediately begin CPR and ventilate patient via BVM at 15 lpm.

3. Initiate basic airway management, per applicable protocols.

4. Transport immediately to the closest open trauma center. Notify receiving facility en route.

FIG. 25

ACUTE CARE TREATMENT SYSTEMS DASHBOARD

CROSS-REFERENCE TO RELATED APPLICATIONS

This application is a continuation under 35 U.S.C. § 120 of U.S. patent application Ser. No. 16/824,763, filed on Mar. 20, 2020, and issued as U.S. Pat. No. 11,759,152, which is a continuation of U.S. patent application Ser. No. 16/399,827, filed on Apr. 30, 2019 and issued as U.S. Pat. No. 10,959,683, which is a continuation of U.S. patent application Ser. No. 13/294,947, filed on Nov. 11, 2011 and issued as U.S. Pat. No. 10,485,490, which claims priority under 35 U.S.C. § 119(e) to U.S. Provisional Patent Application Ser. No. 61/412,679, filed on Nov. 11, 2010, and to U.S. Provisional Patent Application Ser. No. 61/413,266, filed on Nov. 12, 2010, and to U.S. Provisional Patent Application Ser. No. 61/436,943, filed on Jan. 27, 2011, all of which are incorporated herein by reference in their entireties for all purposes.

TECHNICAL FIELD

Embodiments of the present invention relate generally to tools for facilitating acute care treatment, and more specifically to systems and methods for clinical decision support and differential diagnosis.

BACKGROUND

In the pre-hospital and acute care treatment setting, medical responders often have difficulties in accurately determining the proper diagnosis of a particular patient. Even well-trained physicians often have difficulty under emergency conditions in which split second decisions are required with limited information. Computer-automated diagnosis was developed to improve the accuracy, effectiveness, and reliability of both field and hospital of patient treatment.

Automated differential diagnosis utilizes computer inference algorithms such as Bayesian algorithms, neural networks, or genetic algorithms. According to a Wikipedia posting:

The Bayesian network is a knowledge-based graphical representation that shows a set of variables and their probabilistic relationships between diseases and symptoms. They are based on conditional probabilities, the probability of an event given the occurrence of another event, such as the interpretation of diagnostic tests. Bayes' rule helps us compute the probability of an event with the help of some more readily information and it consistently processes options as new evidence is presented. In the context of CDSS [(clinical decision support system)], the Bayesian network can be used to compute the probabilities of the presence of the possible diseases given their symptoms. Some of the advantages of Bayesian Network include the knowledge and conclusions of experts in the form of probabilities, assistance in decision making as new information is available and are based on unbiased probabilities that are applicable to many models. Some of the disadvantages of Bayesian Network include the difficulty to get the probability knowledge for possible diagnosis and not being practical for large complex systems given multiple symptoms. The Bayesian calculations on multiple simultaneous symptoms could be overwhelming for users. Example of a Bayesian network in the CDSS context is the Iliad system which makes use of Bayesian reasoning to calculate posterior probabilities of possible diagnoses depending on the symptoms provided. The system now covers about 1500 diagnoses based on thousands of findings. Another example is the DXplain system that uses a modified form of the Bayesian logic. This CDSS produces a list of ranked diagnoses associated with the symptoms.

Artificial Neural Networks (ANN) is a nonknowledge-based adaptive CDSS that uses a form of artificial intelligence, also known as machine learning, that allows the systems to learn from past experiences/examples and recognizes patterns in clinical information. It consists of nodes called neurodes and weighted connections that transmit signals between the neurodes in a unidirectional fashion. An ANN consists of 3 main layers: Input (data receiver or findings), Output (communicates results or possible diseases) and Hidden (processes data). The system becomes more efficient with known results for large amounts of data. The advantages of ANN include the elimination of needing to program the systems and providing input from experts. The ANN CDSS can process incomplete data by making educated guesses about missing data and improves with every use due to its adaptive system learning. Additionally, ANN systems do not require large databases to store outcome data with its associated probabilities. Some of the disadvantages are that the training process may be time consuming leading users to not make use of the systems effectively. The ANN systems derive their own formulas for weighting and combining data based on the statistical recognition patterns over time which may be difficult to interpret and doubt the system's reliability. Examples include the diagnosis of appendicitis, back pain, myocardial infarction, psychiatric emergencies and skin disorders. The ANN's diagnostic predictions of pulmonary embolisms were in some cases even better than physician's predictions. Additionally, ANN based applications have been useful in the analysis of ECG (a.k.a. EKG) waveforms.

A Genetic Algorithm (GA) is a nonknowledge-based method developed in the 1940s at the Massachusetts Institute of Technology based on Darwin's evolutionary theories that dealt with the survival of the fittest. These algorithms rearrange to form different re-combinations that are better than the previous solutions. Similar to neural networks, the genetic algorithms derive their information from patient data. An advantage of genetic algorithms is these systems go through an iterative process to produce an optimal solution. The fitness function determines the good solutions and the solutions that can be eliminated. A disadvantage is the lack of transparency in the reasoning involved for the decision support systems making it undesirable for physicians. The main challenge in using genetic algorithms is in defining the fitness criteria. In order to use a genetic algorithm, there must be many components such as multiple drugs, symptoms, treatment therapy and so on available in order to solve a problem. Genetic algorithms have proved to be useful in the diagnosis of female urinary incontinence.

Despite the fact that automated differential diagnosis systems have been developed and attempted to be implemented for more than 35 years now, they have not achieved any acceptance in the emergency medical setting for acute care treatment (ACT). In large part, this failure is due to the conditions under which emergency care of acute conditions are practiced. In those situations, such as the treatment of trauma, cardiac arrest or respiratory arrest, speed of decision-making is critical and caregivers already must split their time and attention between the patient and the physiological monitors and defibrillators. In such situations, automated differential diagnosis (ADD) tools are often viewed as interfering with the caregiving process and as a delay to treatment of the patient. Given that every minute can result in a 10% drop in survival rate, such as is the case for cardiac arrest, it is not surprising that ADD tools are ignored by the very people that they were designed to assist.

It has also been found that much of the patient's medical history is inaccessible by the caregiver at the time of the acute medical condition because patients are often treated in the prehospital setting where family members are often not present at the time of the injury.

SUMMARY

Embodiments of the present invention include a system that provides a tool for the caregiver to more efficiently and accurately perform a differential diagnosis that is integrated into the caregivers existing workflow during emergency situations. Embodiments of the present invention may also provide an integrated view of physiological data from the patient, along with therapeutic treatment and patient history and examination findings, in an automated way to caregivers.

A medical system according to embodiments of the present invention includes at least one sensor configured to monitor physiological status of a patient and to generate sensor data based on the physiological status; a user interface device; a processor communicably coupled to the user interface device, the processor configured to: present via the user interface device an array of two or more possible input elements, the input elements each comprising a class of patients or a diagnosis and treatment pathway; receive a selected input element based on a user selection among the two or more possible input elements; acquire the sensor data and process the sensor data to generate physiological data; and present via the user interface device the physiological data according to a template that is customized for the selected input element.

The medical system as described above, in which the selected input element is selected based on activation of one or more switches.

The medical system as described above, in which the selected input element is selected based on touching a touch-activated screen.

The medical system as described above, wherein the touch-activated screen is the user interface screen.

The medical system as described above, wherein the at least one sensor is one or more of an ECG, SpO$_2$, NIR tissue perfusion, NIR pH, ultrasound, ventilator flow rate, EtCO$_2$, invasive blood pressure, and non-invasive blood pressure sensors.

The medical system as described above, wherein the processor is further configured to receive a caliper gesture signal generated by the touching of two points on the touch-activated screen at the same time with the same hand, and to overlay measurement data onto the physiological data upon receipt of the caliper gesture signal.

The medical system as described above, wherein the array of two or more possible input elements includes at least one of: a respiratory distress or dyspnea diagnosis and treatment pathway; an altered mental status diagnosis and treatment pathway; a cardiac distress diagnosis and treatment pathway; a trauma diagnosis and treatment pathway; and a pain or abnormal nerve sensation diagnosis and treatment pathway.

The medical system as described above, wherein the array of two or more possible input elements includes: a respiratory distress or dyspnea diagnosis and treatment pathway; an altered mental status diagnosis and treatment pathway; a cardiac distress diagnosis and treatment pathway; a trauma diagnosis and treatment pathway; and a pain or abnormal nerve sensation diagnosis and treatment pathway.

The medical system as described above, further comprising a tablet computer.

The medical system as described above, wherein the processor is part of the tablet computer.

The medical system as described above, wherein the tablet computer is an iPad® tablet computer.

The medical system as described above, wherein the user interface screen is part of the tablet computer.

The medical system as described above, further including a defibrillator.

The medical system as described above, wherein the user interface screen is part of the defibrillator.

The medical system as described above, wherein tablet computer includes a protective housing, wherein the protective housing includes a first mounting feature, the medical system further including a second mounting feature configured to interfit with the first mounting feature.

The medical system as described above, wherein the array of two or more possible input elements comprises a respiratory distress or dyspnea diagnosis and treatment pathway.

The medical system as described above, wherein the at least one sensor is configured to monitor heart sounds of the patient.

The medical system as described above, wherein the at least one sensor is configured to monitor breathing sounds of the patient.

The medical system as described above, wherein the processor is further configured to differentiate between wheezing, crackles, rale, and stridor breathing sounds.

The medical system as described above, wherein the at least one sensor is a near infrared based sensor.

The medical system as described above, wherein the at least one sensor is configured to measure pH of either tissue or blood of the patient.

The medical system as described above, wherein the at least one sensor is an ECG sensor, and wherein the physiological data reflects heart rate variability.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5 is a table describing a differential diagnosis outline for acute dyspnea in adults.

FIG. 6 is a table describing clues to the diagnosis of dyspnea.

FIG. 7 is a table listing physical examination findings in the diagnosis of acute dyspnea.

FIG. 13 illustrates an example trauma assessment protocol.

FIG. 14 illustrates an example rapid trauma assessment protocol.

FIG. 15 illustrates an example focused physical exam protocol.

FIG. 16 illustrates an example amputation injuries protocol.

FIG. 17 illustrates an example bleeding control protocol.

FIG. 18 illustrates an example burns protocol.

FIG. 19 illustrates an example electrocution protocol.

FIG. 20 illustrates an example spinal immobilization protocol.

FIG. 22 illustrates an example multi-system trauma protocol.

FIG. 23 illustrates an example near drowning protocol.

FIG. 24 illustrates an example trauma in pregnancy protocol.

FIG. 25 illustrates an example traumatic cardiac arrest protocol.

Figure 1:
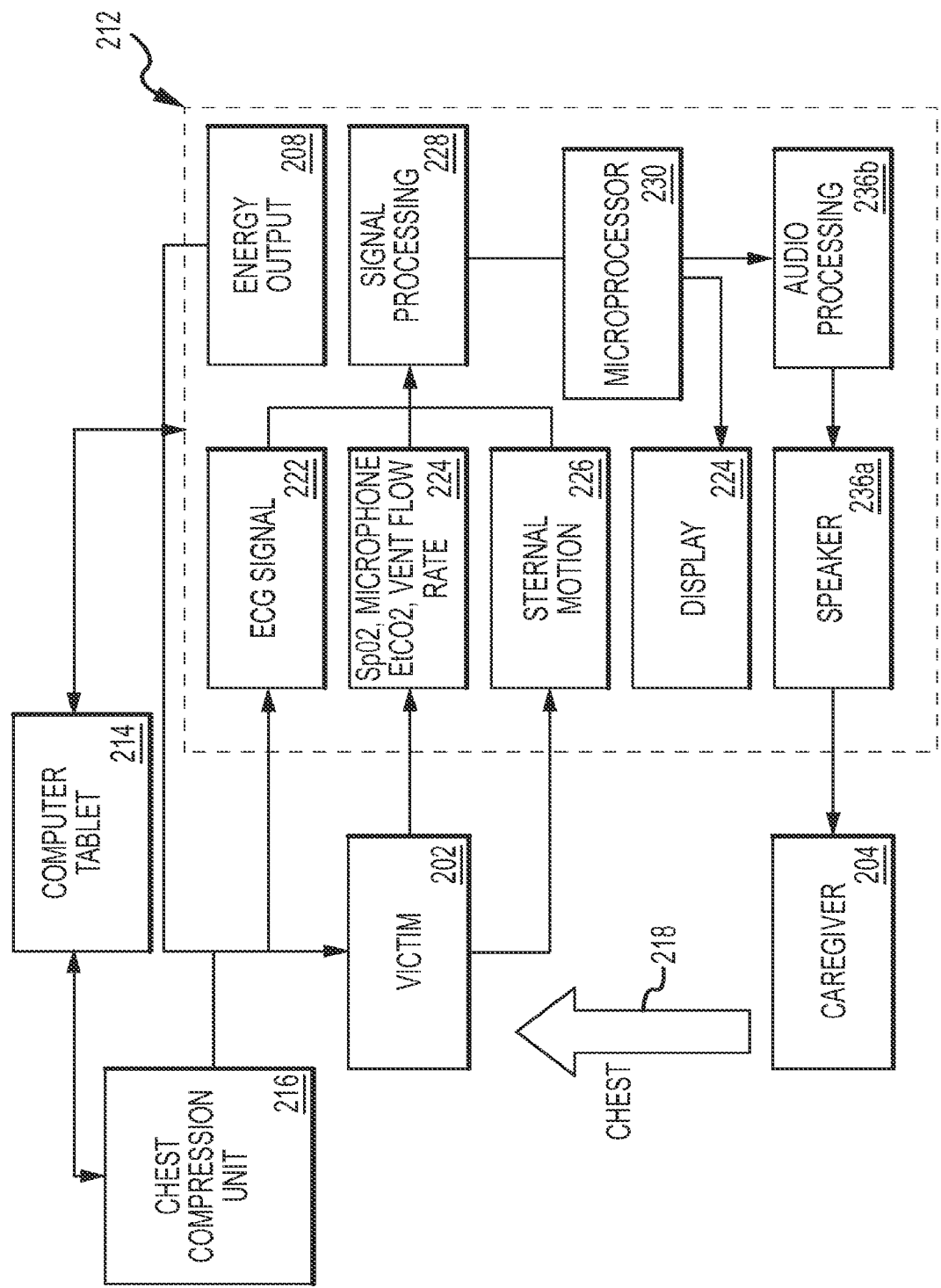
FIG. 1 illustrates a clinical decision support system, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
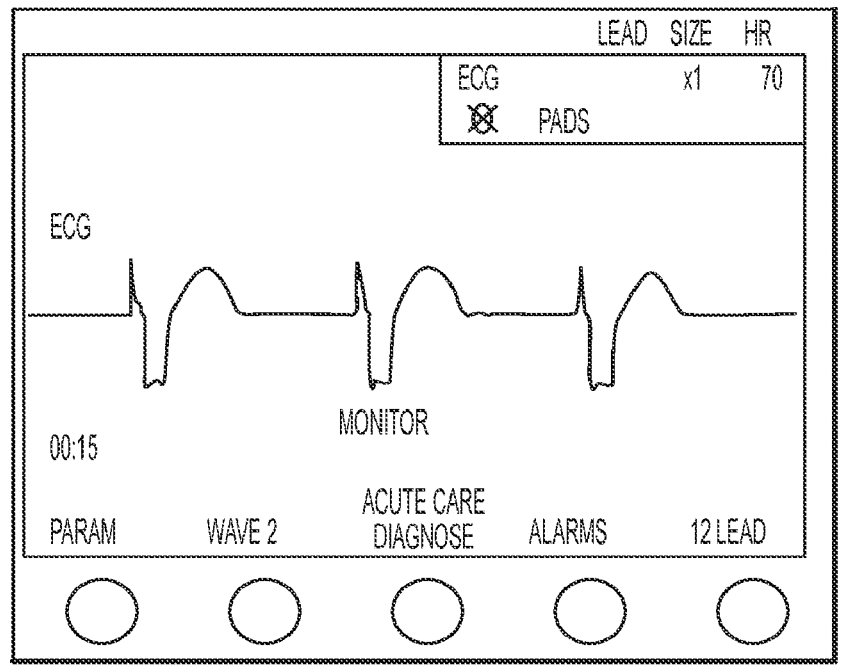
FIG. 2 illustrates a user interface for a medical device, according to embodiments of the present invention.

FIG. 1 shows a block diagram of the system, according to embodiments of the present invention. In one embodiment, a combined defibrillator/monitor device such as the E-Series manufactured by ZOLL Medical of Chelmsford Massachusetts has keys whose labeling is provided by on-screen text. The text is thus configurable in real time ether due to input by the user or as a result of analysis and decision making by the defibrillator or other devices with which the defibrillator is in communication at the time of the defibrillator's use, such as the computer tablet device 214 or remote base station staffed by medical dispatch or medical supervisory personnel in communication with the computer tablet. The computer tablet may take the form of an iPad (Apple Corp., Cupertino CA). Such screen-labeled keys may be referred to as "soft-keys". A specific soft-key is initially labeled "Acute Care diagnose" at device turn-on as shown in FIG. 2, according to embodiments of the present invention. Upon detecting a key press of the Acute Care Diagnose key, the defibrillator changes the functionality and labeling of the keys to those shown in FIG. 3. These five labels—"Respiratory Distress" or alternatively "Dyspnea", "Altered Mental Status", "Cardiac Distress", "Trauma" and "Pain/Abnormal Nerve Sensation"—differ from the traditional symptoms associated with differential diagnosis in that they identify classes of patients and potential workflows and diagnosis and treatment pathways (DTP), and are listed in relative frequency with which paramedics and other emergency personnel encounter patients meeting these criteria in actual practice.

Figure 4:
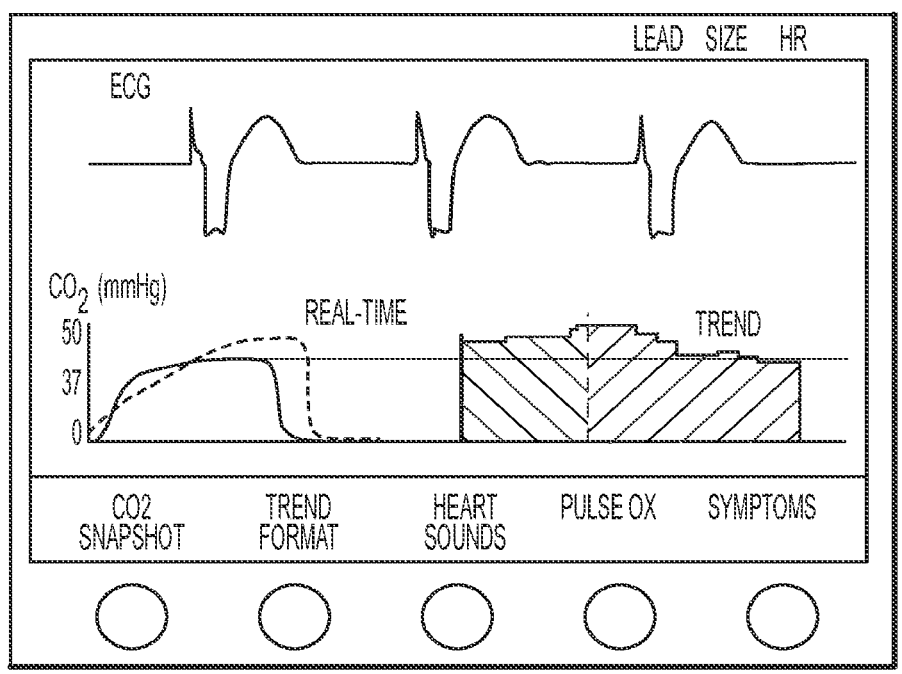
FIG. 4 illustrates the user interface of FIGS. 2 and 3 upon selection of a respiratory distress mode, according to embodiments of the present invention.

By pressing the soft-key for each DTP, the defibrillator is then configured to potentially activate certain physiological sensors and display the sensor data in such a way as to provide the caregiver the optimal information, presented in the optimal fashion so as to diagnose and treat the patient most accurately and efficiently. Each DTP may include a template according to which sensor data, or the physiological and/or measurement data derived therefrom, is displayed in a way most useful and/or efficient for that particular DTP. For instance, if the "Respiratory Distress" soft-key is pressed, then the waveforms and numeric physiologic data on the screen change to that shown in FIG. 4. Stored snapshots of individual $CO2$ breath waveforms may be initiated via the $CO2$ Snapshot soft-key. These snapshots remain on the display for reference to the clinician both for automating measurements for diagnosis as well as for assessing the effectiveness of a particular therapy.

Figure 8A:
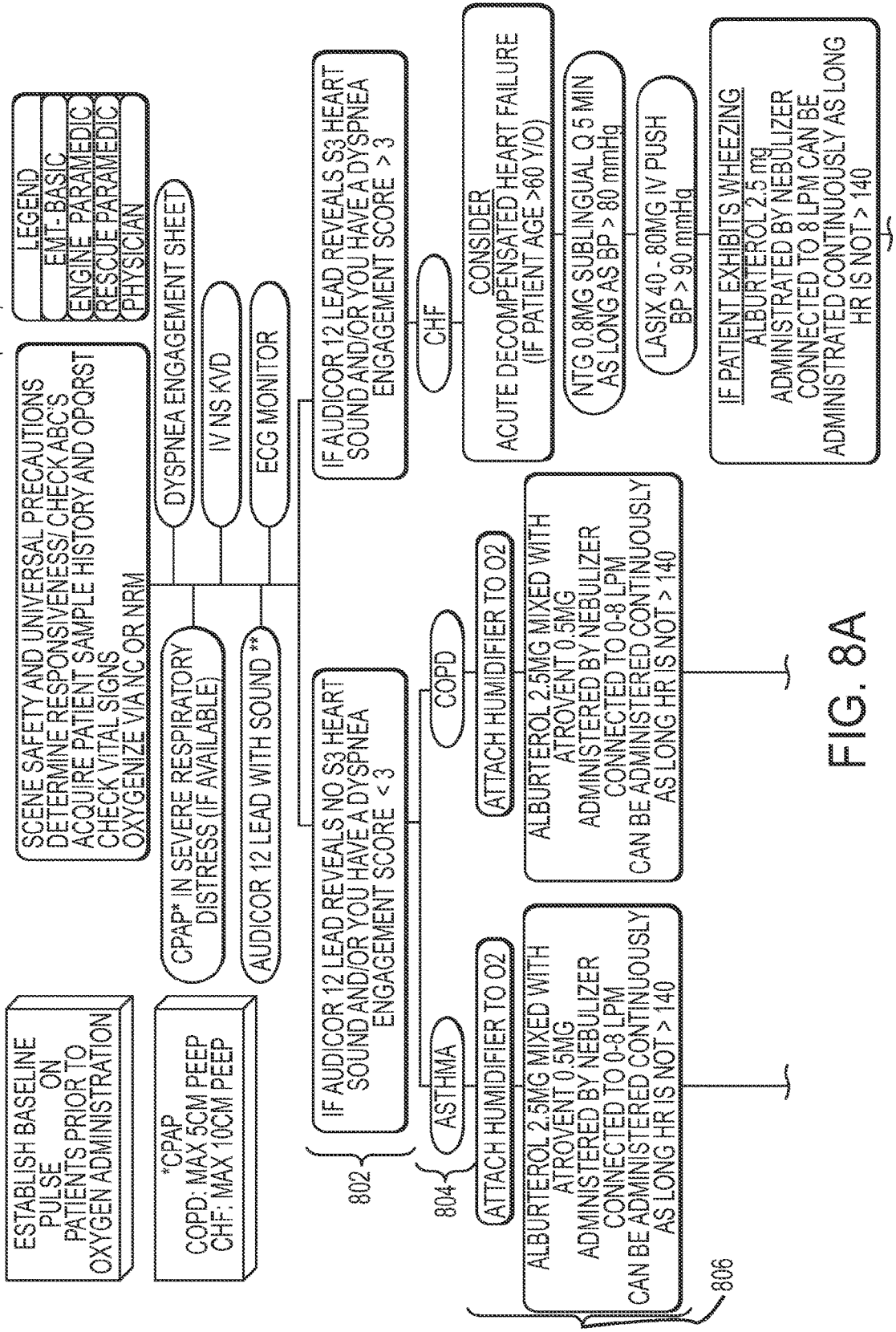
FIG. 8A is a top portion of a common medical protocol and differential diagnosis flow chart for adult shortness of breath.
Figure 8B:
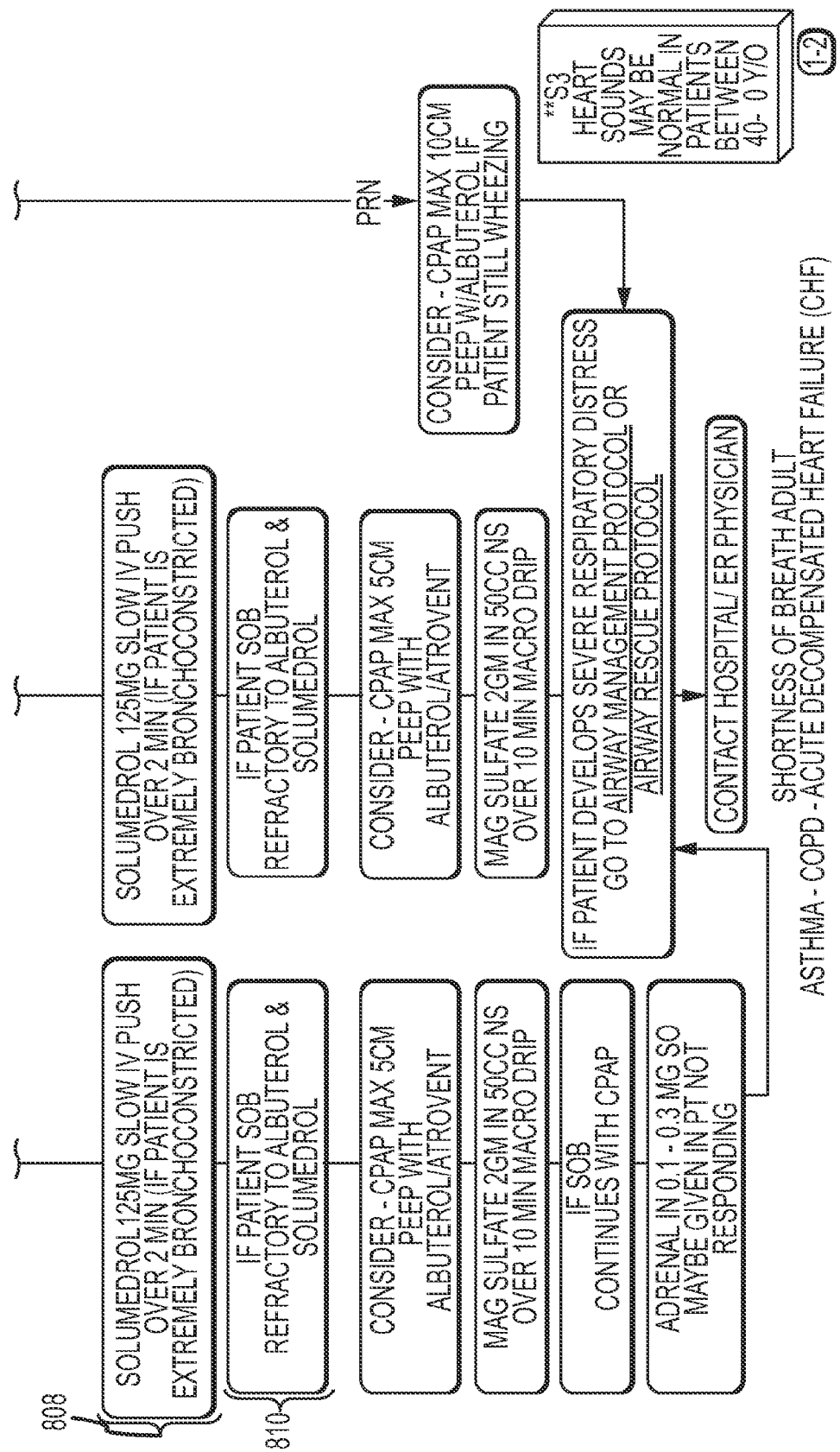
FIG. 8B is a continuation of the common medical protocol and differential diagnosis flow chart of FIG. 8A.
Figure 9:
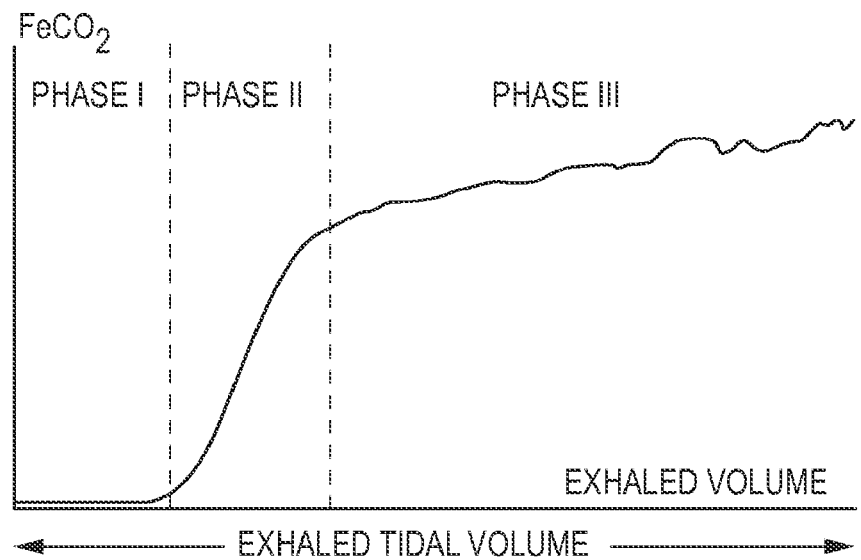
FIG. 9 illustrates a carbon dioxide snapshot waveform which may be displayed on the user interface when selected by the user, according to embodiments of the present invention.

Heart sound measurement and detection may be incorporated into the monitoring device for the detection of S3 and S4 heart sounds and automatically narrow the differential, or suggest for the rescuer to confirm agreement with the software diagnosis, of heart failure or pulmonary edema. A flowchart for evaluating heart sounds is shown in FIGS. 8A and 8B. Pulse oximetry and capnography are also very helpful measures and may be automatically incorporated into the algorithm for more accurate diagnosis. The same sensors used to detect heart sounds may also be employed to detect breath sounds and to analyze their quality. Specific algorithms may be employed to detect wheezing, crackles, rale or stridor, each of which may be indicative of a particular disease.

Sensors such as flow sensors and O2 gas sensors are included in some embodiments, so that the additional physiological measurements such as volumetric Co2, volumetric O2 and spirometry, which are relevant for diagnosis and treatment of dyspnea, may be included and displayed on the Respiratory Distress DTP screen. An oxygen sensor may be located in the patient's airway, which may assist in calculating the metabolic needs of the patient.

Figure 10:
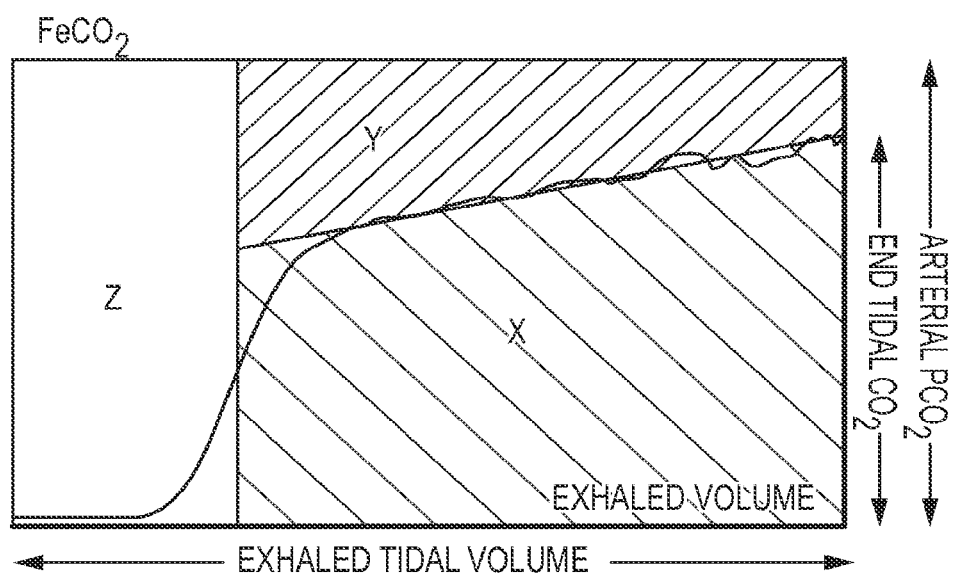
FIG. 10 illustrates the carbon dioxide snapshot waveform of FIG. 9 with displayed measurements, according to embodiments of the present invention.

The display on the defibrillator 212 is a touchscreen, according to some embodiments of the present invention. The caregiver can easily initiate measurements such as on the $CO2$ snapshot waveform or the spirometry snapshot waveform via touchscreen gesture such as a double tap. A zoom icon may exist in the upper corner of each waveform box, such as the $CO2$ snapshot, such that when the zoom button is touched, that particular waveform fills the display of the defibrillator. Another measurement button is present which, when touched, displays all the relevant measurements for a particular waveform, according to embodiments of the present invention. A gestural interface is provided as part of the touchscreen. Using two fingers or finger and thumb to touch to two points in the waveform (which may also be referred to as a "caliper" measurement or gesture) will cause measurements to be displayed and/or overlaid onto the physiological data, as illustrated in FIG. 10. For instance, dead space volume, phase II and III slopes which are indicative of COPD, and estimates of arterial pCO2 may be listed on the screen after initiation of CO2 waveform measurement.

According to embodiments of the present invention, the processor communicably coupled with the touchscreen portion of a decision support system may be configured to recognize the wave shape of a wave signal being displayed, and/or recognize the edge of an image being displayed, in order to improve the accuracy of a caliper touch gesture. For example, if a user were to use a caliper gesture to measure or "zoom in" on an ST elevation in an ECG wave display, the decision support system may be configured to recognize that if one of the user's fingers taps just below the top of the ECG wave, that the user likely intended to include the top of the ECG wave in the enlarged or selected view. In addition, the decision support system may be configured to permit an ability to enlarge (zoom) and adjust measurement points individually using the touchscreen. A tap/click and drag method may be used to set the caliper gesture; for example, to hone in on a particular portion of displayed waveform, the user may press on one point and drag to another point to indicate the endpoints of the caliper gesture.

Specific out-of-range readings can be displayed in red or highlighted by other mechanisms, such as bold-face font and/or flashing. Touching the highlighted values will cause the display to show the possible diagnoses which are consistent with the measurements, according to embodiments of the present invention. A specific graphical zone of the screen can be designated with a graphical image of the computer tablet. By dragging waveforms, measurements, or any other data object shown on the display over onto the computer tablet icon, it can automatically be presented on the computer tablet that is linked to the defibrillator.

Capnography is helpful in the assessment of asthma, where an increased slope in the expiratory plateau provides a measure of bronchospasm. The slope of the plateau phase (phase III) provides a measure of airway obstruction. The adequacy of b-agonist bronchodilatory therapy for an asthma exacerbation may be monitored through observation of slope change of phase III.

As referenced in U.S. Patent Application Publication No. 2011/0172550, published on Jul. 14, 2011, which is incorporated by reference herein in its entirety for all purposes, the data for the patient's history may be entered via the computer tablet with patient physiological measures via the monitor. As the differential diagnosis often implicates both patient history, patient examination findings along with measures of the patient's physiological state via such monitoring as ECG, capnography and pulse oximetry, these data elements are integrated into a user interface that automatically or semi-automatically integrates the various data elements on a single differential diagnosis screen within the application on the computer tablet. The interface may begin by asking the rescuer to choose from a list of common presenting symptoms or complaints by the patient, for example dyspnea or respiratory distress. The information such as on the screens of FIGS. 5, 6, and 7 (taken from Am Fam Physician 2003; 68:1803-10) provides one possible structured approach for rescuers to obtain information. As patient history and physical examination findings are entered on the computer tablet, the differential diagnosis page will gradually narrow down the possible diagnoses.

Figure 11:
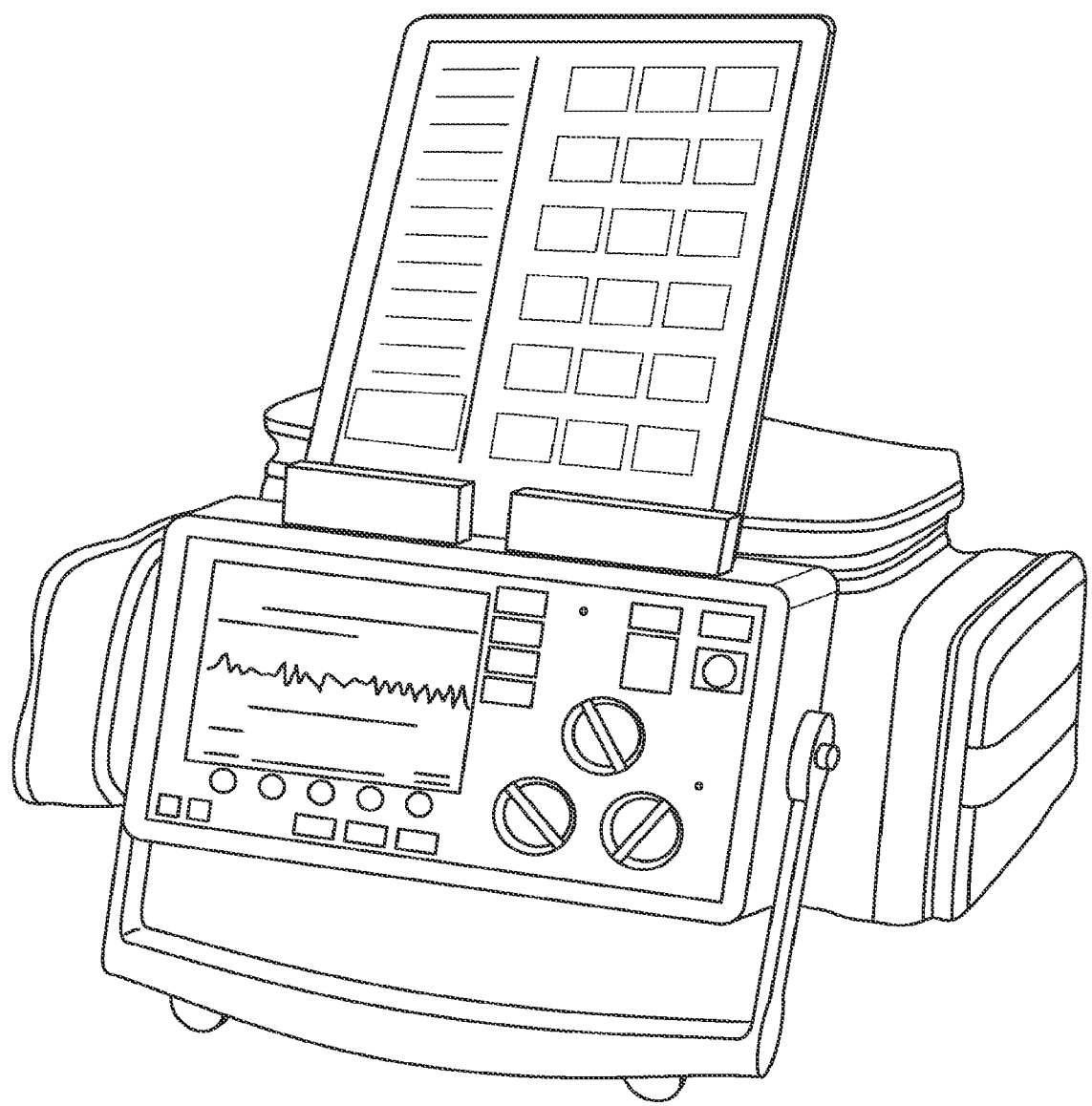
FIG. 11 illustrates a tablet computing device docked on a defibrillator device, according to embodiments of the present invention.

In another embodiment, the defibrillator contains a docking feature for propping up a computer tablet such as an Apple® iPad® on top of the defibrillator in a stable position via mounting features integrated onto the defibrillator, as illustrated in FIG. 11. Other mobile computing devices, including tablet computers, an iPhone®, an iTouch®, and other touchscreen monitors may be used. Alternatively, a low power, battery powered, touchscreen monitor may be used, such as, for example, those that transfer information to and from a computing device via a wired or wireless USB connection. Communication may be provided wirelessly between the two devices (the medical device and the mobile computing device, for example). Other communicable coupling may be achieved between the two devices; for example, wired. The iPad may include a protective housing and/or waterproof housing to protect it from the typical physical abuse it would likely encounter in the prehospital environment. Mounting features integral to such an iPad housing allow it to be easily attached on top of the defibrillator on scene. The mounting feature on the defibrillator may be able to hinge to allow the iPad® to hinge down when not in use into a protective pocket on the defibrillator. The iPad® may also be undocked and used nearby to the defibrillator, without need for physical connection. A physical slot may also be provided, preferably at the side, top or back of the unit that allows for the iPad® to have its battery charged by the defibrillator. Internal to the frame of the iPad® protective housing is the standard iPad® connector, while on the exterior of the frame of the iPad® protective housing are much more robust mechanical and electrical connections that can withstand the extensive abuse experienced by medical devices in the prehospital emergency setting, according to embodiments of the present invention.

The results of this integrated analysis of physiological data, patient history and examination findings may then be displayed on the defibrillator, potentially in the form of asking to make an additional physiological measurement. The results of this integrated analysis of physiological data, patient history and examination findings may alternatively, or additionally, be displayed on the tablet computer. According to some embodiments of the present invention, the tablet computer, or other mobile computing device, may be communicably coupled with the defibrillator or other physiological assessment device, for example through a wireless connection. As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network, or direct coupling.

According to embodiments of the present invention, a user interface device is communicably coupled to a processor, and the processor is configured to receive data entered via the user interface device, as well as data received from one or more sensors, in order to perform clinical decision support based on both data sources. The user interface device may include one or more devices such as a touch screen computer, a tablet computer, a mobile computing device, a smart phone, an audio receiver, an audio transmitter, a video receiver, a video transmitter, a camera, and a "heads up" display projected onto a user's glasses or face shield. A small monitor may be mounted onto eyeglasses, a face shield, and/or integrated with other wearable communications devices, such as, for example, an ear bud or a Bluetooth® hands free phone adaptor. The user interface device may include a combination of devices for conveying options and receiving input; for example, an audio speaker may be used to convey possible DTPs, and an audio receiver may be used to receive a verbal command indicating a selection of one of the DTPs. Instead of an audio receiver, a video camera may be used to receive a gestural command that will be interpreted by the processor as a selection of one of the possible DTPs, or input elements. Using hands-free devices for user interface devices may free the hands of a caregiver to perform clinical tasks, while still permitting non-intrusive decision support and/or differential diagnosis for the caregiver.

FIGS. 8A and 8B illustrate a differential diagnosis and/or clinical support process through which a computer processor may take a caregiver, using the user interface device, according to embodiments of the present invention. For example, if the caregiver selected "Respiratory Distress" from among the five DTPs presented on the screen of FIG. 3, then the user interface device would prompt the caregiver to input information about step 802 in the flowchart of FIG. 8, which flows from top to bottom. At step 802, if the 12-lead reveals an S3 heart sound, or if the Dyspnea Engagement Score is greater than 3, then the decision support system will take the user through the Acute Decompensated Heart Failure (CHF) decision/diagnosis process.

The decision support system may take into account both physiological data received from sensors, and information data received from the caregiver (e.g. via mobile computing device such as an iPad®), in helping the caregiver move from one decision point in the flow chart to the next, while updating any display or information provided along the way. For example, the decision support system may indicate to the user that, based on processing of the ECG data, there does not appear to be an S3 heart sound present, and ask the caregiver to confirm this assessment. The decision support system may also, or alternatively, request the caregiver to enter a Dyspnea Engagement Score, or suggest one for confirmation by the caregiver. At step 802, if the 12-lead reveals no S3 heart sound, or if the Dyspnea Engagement Score is less than 3, then the decision support system will recognize that the caregiver is not dealing with a CHF situation, but then moves to step 804 in which the decision support system changes its display and/or input prompts in order to help the caregiver determine whether to enter the Asthma treatment path or the COPD treatment path.

Again, the decision support system may factor in various physiological data from sensors, as well as various informational data received about the particular patient, in helping to support the caregiver's decision. For example, as illustrated in FIG. 6, if the patient information (either entered by the caregiver or obtained from another source) indicates that the patient is involved in heavy tobacco use, the decision support system will recognize at step 804 that a COPD diagnosis is more likely, whereas if the caregiver indicates to the decision support system that the patient is experiencing a cough, or has a history of asthma, the decision support system may recognize at step 804 that an Asthma diagnosis is more likely. In addition to, or alternatively to, the informational diagnosis support reflected in FIG. 6, the decision support system may gather findings using physiological data to help the caregiver determine the appropriate treatment path. For example, if a breathing or breath sound sensor generates data that, when processed, indicates clubbing, barrel chest, or decreased breath sounds, the decision support system may recognize at step 804 that a COPD treatment path is more appropriate, whereas if the breath sound sensor generates data indicative of pulsus paradoxus, or if a muscle activity sensor indicates accessory muscle use, the decision support system may recognize at step 804 that an Asthma treatment path is more appropriate.

According to embodiments of the present invention, the decision support system may suggest or propose a diagnosis or treatment path, for example by indicating statistical probabilities (based on charts and data such as those of FIGS. 6 and 7) or relative likelihoods, and ask for confirmation or final selection by the caregiver. For example if at step 804 the decision support system receives confirmation of an Asthma diagnosis, then the user interface device may change the information presented to the caregiver, for example by launching into a treatment protocol specific to the Asthma diagnosis. At step 806, the decision support system may suggest that the caregiver attach a humidifier to the patient's oxygen supply, and administer 2.5 milligrams of albuterol mixed with 0.5 milligrams of Atrovent administered by nebulizer connected to a 6-9 liter per minute source, and may indicate that the dosage may be administered continuously as long as the heart rate is not greater than 140. The decision support system may monitor the heart rate, and give a visual and/or audio indication when and if the heart rate reaches or approaches 140, in this example.

At step 808, the decision support system may help the caregiver decide whether the patient is extremely bronchoconstricted, for example by showing data or measurements related to blood oxygen content, respiration rate, or respiration volume. Upon a confirmation by the caregiver that the patient is extremely bronchoconstricted at step 808, the decision support system may then suggest to the caregiver that a 125 milligram dose of Solumedrol be administered over a slow (e.g. 2 minute) intravenous push. At step 810, the decision support system may help the caregiver to decide whether the patient's symptoms have improved (e.g. whether the patient's shortness of breath has improved with the treatment thus far). For example, the decision support system may display and/or analyze the patient's end-tidal waveform, and suggest that the patient does not appear to be responding to the treatment, and ask for the caregiver's confirmation. If the caregiver confirms the decision, then the decision support system may continue to guide the caregiver through additional treatment options, for example those indicated in FIG. 8. In this way, the decision support system guides the caregiver through complex decision making processes, during the clinical encounter, using both physiological data and informational data gathered from the patient or input by the caregiver, in a way which would be too inconvenient or time-consuming for the caregiver to perform absent the decision support system.

The decision support according to embodiments of the present invention may or may not be fully automated. Inference engines utilizing Bayesian networks, neural networks, genetic algorithms, or simpler rule-based systems may be employed.

In another embodiment, the tissue CO2 or pH are measured by methods such as those described in U.S. Pat. No. 6,055,447, which describes a sublingual tissue CO2 sensor, or U.S. Pat. Nos. 5,813,403, 6,564,088, and 6,766,188, which describe a method and device for measuring tissue pH via near infrared spectroscopy (NIRS), and which are all incorporated herein by reference in their entirety for all purposes. NIRS technology allows the simultaneous measurement of tissue PO2, PCO2, and pH. One drawback of previous methods for the measurement of tissue pH is that the measurements provided excellent relative accuracy for a given baseline measurement performed in a series of measurements over the course of a resuscitation, but absolute accuracy was not as good, as a result of patient-specific offsets such as skin pigment. One of the benefits achieved by some embodiments of the present invention is the elimination of the need for absolute accuracy of these measurements, and the reliance on only the offset and gain being stable over the course of the resuscitation. Tissue CO2 and pH are particularly helpful in monitoring in the trauma DTP. Physiological parameters on display for the trauma DTP may be one or more of: invasive and non-invasive blood pressure, tissue CO2 and pH, ECG, SpO2 trending, and heart rate variability risk index. The ECG may be analyzed to determine the interval between adjacent R-waves of the QRS complexes and using this interval to calculate heart rate variability as a running difference between adjacent R-R intervals. It is known to those skilled in the art that an abrupt reduction in variability will often precede by many minutes a precipitous decline in a patient's blood pressure (traumatic arrest). By monitoring the trend in heart rate variability, the traumatic arrest can be anticipated and prevented.

Figure 12:
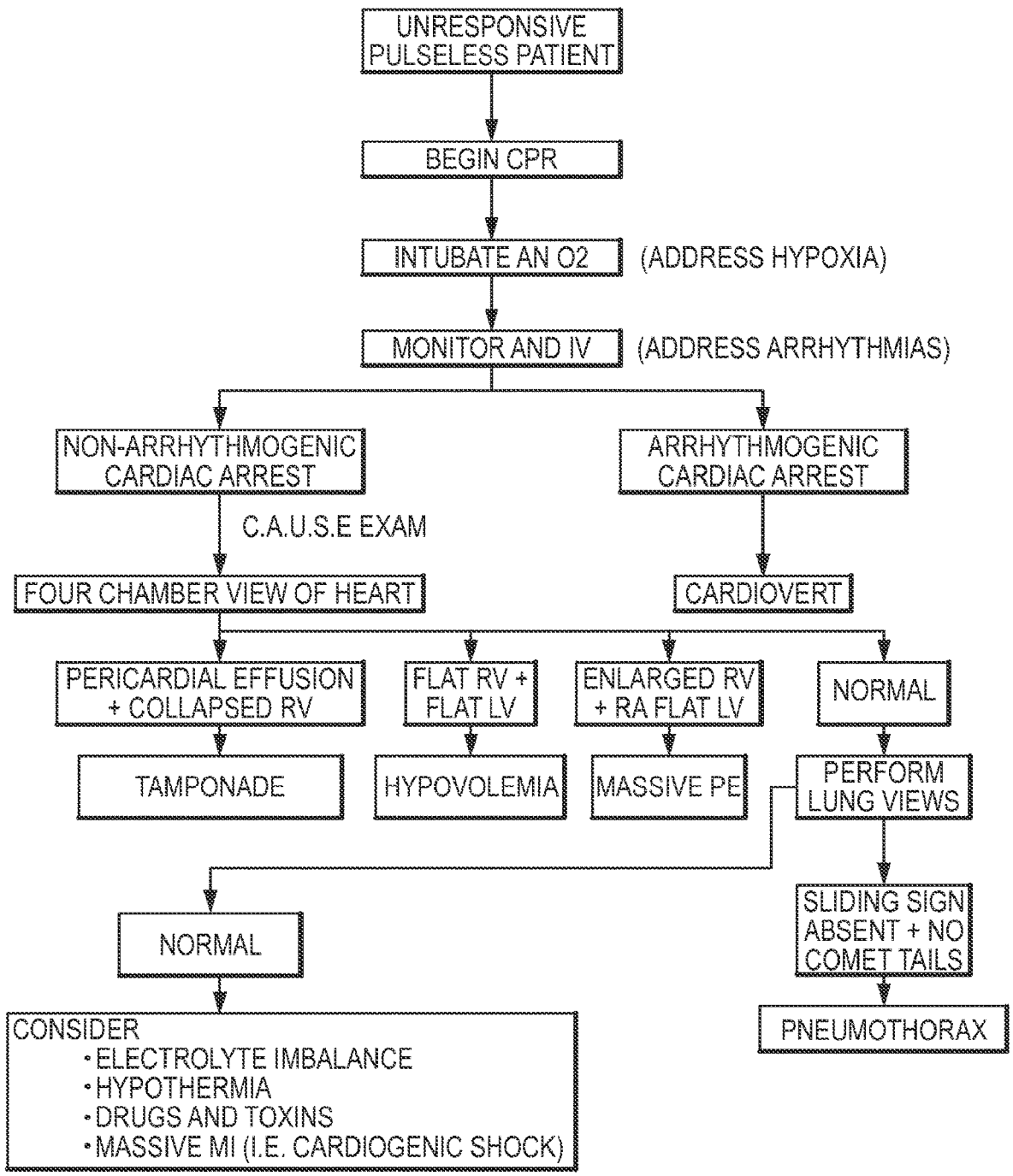
FIG. 12 illustrates a protocol for use in patients with cardiac arrest.
Figure 21:
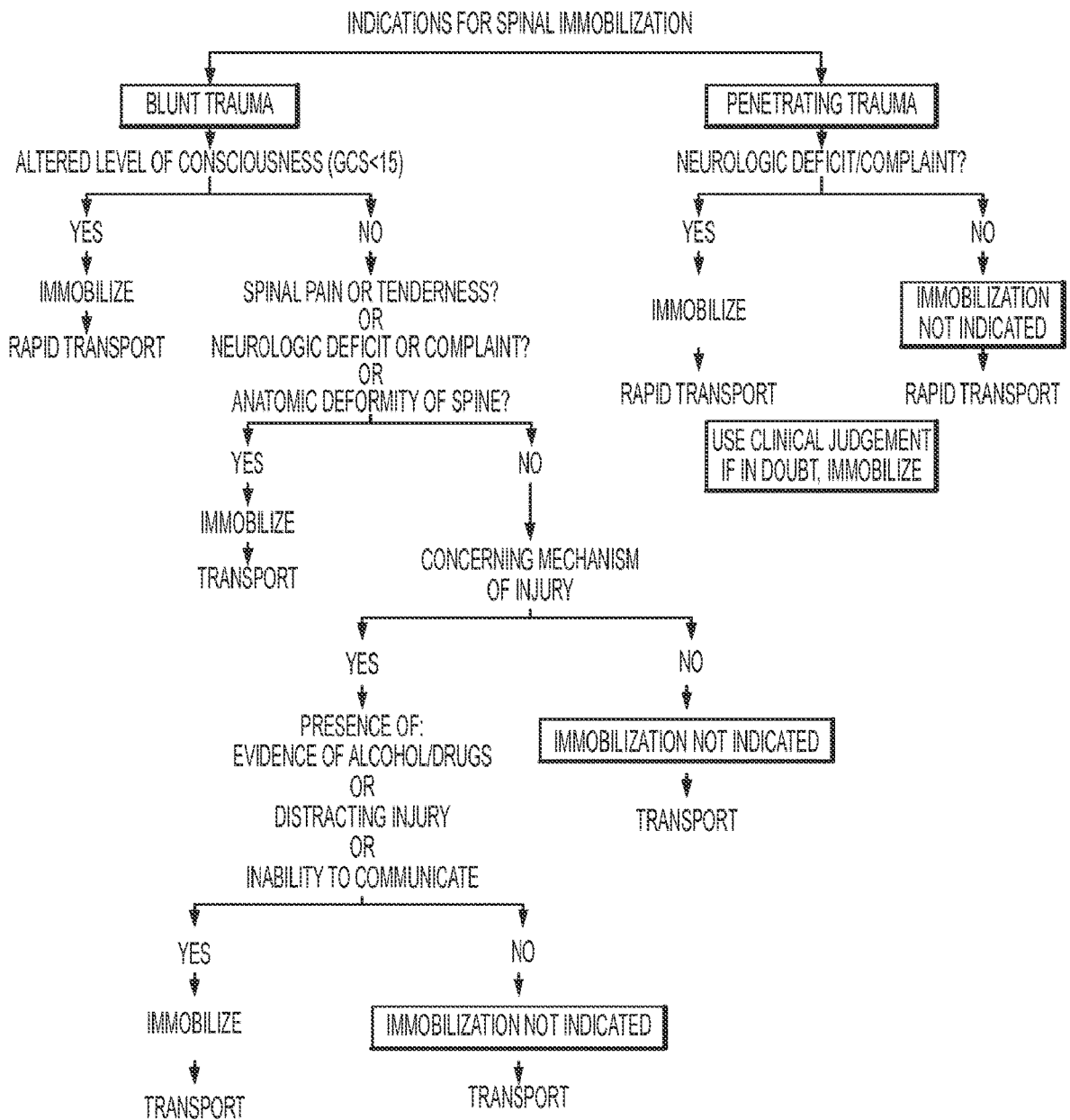
FIG. 21 illustrates additional steps in the spinal immobilization protocol of FIG. 20.

Another sensor of use for the trauma DTP is ultrasound, according to embodiments of the present invention. According to C. Hernandez et al., C.A.U.S.E.: *Cardiac arrest ultra-sound exam—A better approach to managing patients in primary non-arrhythmogenic cardiac arrest*, Resuscitation (2007), doi:10.1016/j.resuscitation.2007.06.033, which his incorporated by reference herein in its entirety for all purposes:

C.A.U.S.E. is a new approach developed by the authors. The C.A.U.S.E. protocol addresses four leading causes of cardiac arrest and achieves this by using two sonographic perspectives of the thorax; a four-chamber view of the heart and pericardium and anteromedial views of the lung and pleura at the level of the second intercostal space at the midclavicular line bilaterally. The four-chamber view of the heart and pericardium is attained using either the subcostal, parasternal or apical thoracic windows. This allows the individual performing the examination to select the most adequate view depending on the patients' anatomy. The authors recommend beginning with the subcostal view first as this view makes it possible for the practitioner to evaluate the heart without interrupting chest compression. If this view is not possible then the apical or parasternal approaches may be used during coordinated pulse checks lead by the resuscitation team leader. A four-chamber view is used in this protocol as it allows for ease of comparison between the different chambers in the heart, facilitating the diagnosis of hypovolemia, massive PE, and cardiac tamponade (FIG. 6). Pneumothorax is diagnosed by identifying the lack of sliding sign and comet-tail artifact while looking in the sagital plane at the second intercostal space of the midclavicular line (FIG. 7). For both the cardiac and lung views it is recommended to use a 2.5-5.0 phased array transducer probe. This allows the examiner to use the same probe for both lung, heart and if needed abdominal exam. This type of probe was used by Knudtson in his study involving ultrasound for the use of identifying pneumothorax as an addition to the FAST exam, and it yielded very a high accuracy in detecting pneumothorax, yet still remained useful in identifying the heart and abdominal organs. The protocol is best described in diagram form. [see FIG. 12]

The caregiver selecting elements of the flowchart results in the ultrasound sensor being activated and images presented on the computer tablet. Additional instructions can be requested from the interface on either the computer tablet and/or the defibrillator. Based on the selections and instructions, the settings of the ultrasound can be adjusted to deliver the optimal images, according to embodiments of the present invention.

Figure 3:
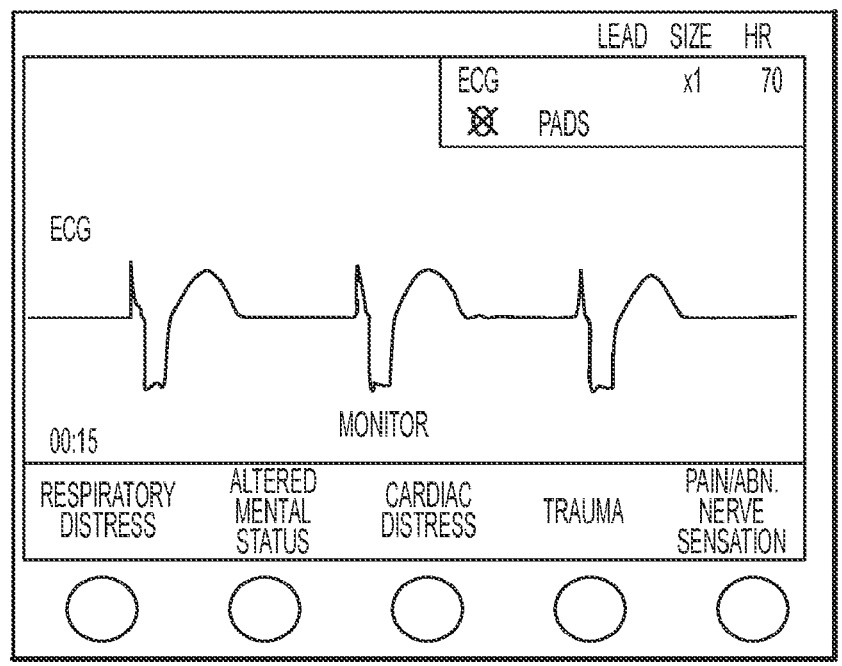
FIG. 3 illustrates the user interface of FIG. 2 upon selection of an acute care diagnosis mode, according to embodiments of the present invention.

Although five diagnosis and treatment pathways are discussed with respect to FIG. 3, the differential diagnosis/decision support system may be configured to support decision making and diagnosis with respect to other DTPs, and may be configured to display and support various combinations of one or more DTPs, from among the five shown in FIG. 3 and others. According to other embodiments of the present invention, each user may configure the decision support system to use customized DTP for each DTP option; for example, the user may change the default series of questions/steps/readings for the Trauma DTP with a new series of questions/steps/readings based on caregiver-specific, patient-specific, geography-specific, and/or regulation-specific treatment protocols. In this way, the decision support system according to embodiments of the present invention operates to guide decision making and diagnosis for a caregiver in a way that accommodates various kinds of DTPs.

For example, if a user selected the Trauma DTP option from the screen of FIG. 3, the decision support system may be configured to guide a user through a decision and treatment pathway similar to that shown in FIGS. 13-25. The user would then be presented with a series of further options, such as "amputation injury," "bleeding control," "burns," and the like. Selecting one of these further options would then cause the decision support system to enter and display the particular pathway or pathways relevant to the selected option. According to embodiments of the present invention, the decision support system is comprised by a user interface device, independent of a medical device or one or more sensors, in a way which simply guides the caregiver through a series of decisions according to a pre-established flow chart. At a basic level, a medical device, such as a defibrillator, may include one or more decision support flow charts and/or treatment protocols, which guide the caregiver through various decisions, either with or without sensor data or other data input. A graphical DTP may be included in a defibrillator device as a reference document, electronically navigable.

According to other embodiments, the decision support system is informed by a combination of caregiver observations, patient information, and/or sensor data. Assessment and/or scoring may be performed, either by receiving data from the caregiver, or receiving data from sensors, or both. For example, for a trauma DTP, the decision support system may take into account pulse rate, breathing data, qualitative breathing data, pulse rate, blood loss, blood pressure, presence of broken limbs, and/or compound fractures. Or, in a cardiac distress DTP, the decision support system may be configured to display a cardiac arrest probability at a moment in time, which may be calculated and/or predicated by the decision support system based on selected criteria. The decision support system may also be configured to track certain criteria in order to suggest treatment outcome probabilities, for example suggesting the treatment pathway with the highest or a high perceived probability of success.

According to some embodiments of the present invention, a monitor, or a defibrillator/monitor combination, or other similar device, may be configured to provide a graphical tool to configure the monitor to follow recognized rescue protocols, for example one or more of the protocols described and/or shown herein. Such a tool may be included on the monitor or defibrillator device, on a tablet or handheld or other computing device, and/or on both, according to embodiments of the present invention. Such a tool may be provided in a graphical interface, for example a flowchart. The tool allows the user to configure the patient monitor to follow a particular rescue protocol, for example by visually presenting a flow chart for the protocol and allowing the user to customize the protocol. For example, the length of the CPR period may be configured by the user to customize the treatment protocol. Such a tool may also permit the downloading and uploading of customized treatment protocols to and/or from a monitoring device, which may also permit the same customized protocol settings to be carried on a mobile device and/or transferred or uploaded to multiple other devices in different locations and/or at different times, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A patient monitoring system comprising:
    at least one sensor configured to measure patient data comprising physiologic waveform data;
    at least one ultrasound sensor; and
    a defibrillator configured to couple to the at least one sensor and comprising:
        a touchscreen user interface; and
        at least one processor communicatively coupled to the touchscreen user interface and configured to:
            cause the touchscreen user interface to display sonographic image data and the patient data comprising at least one physiologic waveform based on the physiologic waveform data,
            detect user input comprising a first user touchscreen input and a second user touchscreen input,
            generate a caliper measurement signal that identifies define endpoints of a caliper based on the first user touchscreen input and the second user touchscreen input, wherein the endpoints of the caliper identify a particular portion of the at least one physiologic waveform, and
            cause the touchscreen user interface to display a measurement of the particular portion of the at least one physiologic waveform based on the endpoints of the caliper.

2. The patient monitoring system of claim 1, wherein the at least one physiologic waveform comprises an electrocardiogram (ECG) waveform.

3. The patient monitoring system of claim 2, wherein the particular portion of the at least one physiologic waveform comprises an ST elevation in the ECG waveform.

4. The patient monitoring system of claim 1, wherein the at least one processor is configured to cause the touchscreen user interface to display the measurement as an overlay on the at least one physiologic waveform.

5. The patient monitoring system of claim 1, wherein the first user touchscreen input and the second user touchscreen input comprise taps by two fingers or taps by a finger and a thumb.

6. The patient monitoring system of claim 1, wherein the first user touchscreen input comprises a tap on a first point on the at least one physiologic waveform and the second user touchscreen input comprises a drag to a second point on the at least one physiologic waveform.

7. The patient monitoring system of claim 1,
    wherein the at least one sensor comprises at least one of a flow sensor or an oxygen gas sensor, and
    wherein the patient data comprises at least one of $CO_2$ data, pulse oximetry data, or spirometry data.

8. The patient monitoring system of claim 1, wherein the at least one processor is configured to:
    identify a feature of the at least one physiologic waveform, and
    adjust the particular portion of the at least one physiologic waveform to include the identified feature in the particular portion.

9. The patient monitoring system of claim 8, wherein the at least one processor is configured to adjust the particular portion based on a proximity of the user input to the feature.

10. The patient monitoring system of claim 1, wherein the at least one processor is configured to zoom in on at least one feature of the at least one physiologic waveform in response to the user input to provide an enlarged view of the at least one feature.

11. The patient monitoring system of claim 1, wherein the defibrillator is communicatively coupled to a mobile computing device.

12. The patient monitoring system of claim 11, wherein the mobile computing device comprises one of a tablet computing device or a smartphone device.

13. The patient monitoring system of claim 1, wherein the defibrillator is communicatively coupled to a wearable communications device.

14. The patient monitoring system of claim 1, wherein the at least one processor is configured to cause the touchscreen user interface to display patient history along with the patient data measured by the at least one sensor.

15. The patient monitoring system of claim 1, wherein the at least one sensor comprises a sternal motion sensor.

16. The patient monitoring system of claim 1, wherein the defibrillator is configured to communicatively couple to a remote medical station.

17. The patient monitoring system of claim 1, wherein the at least one sensor comprises one or more of a ventilator flow rate sensor, an invasive blood pressure sensor, or a non-invasive blood pressure sensor.

* * * * *

UNITED STATES PATENT AND TRADEMARK OFFICE
CERTIFICATE OF CORRECTION

Page 1 of 1

PATENT NO. : 12,207,953 B2
APPLICATION NO. : 18/358997
DATED : January 28, 2025
INVENTOR(S) : Gary A. Freeman and Guy R. Johnson It is certified that error appears in the above-identified patent and that said Letters Patent is hereby corrected as shown below:

In the Specification

Column 1, Line 9 delete "2020," and insert --2020--

In the Claims

Claim 1, Column 13, Line 50 before "endpoints" delete "define"

Signed and Sealed this
Eighteenth Day of March, 2025

Coke Morgan Stewart
*Acting Director of the United States Patent and Trademark Office*